United States Patent [19]

Dragan

[11] 4,139,943

[45] Feb. 20, 1979

[54] DOWEL PIN FOR MAKING A DENTAL DIE

[76] Inventor: William B. Dragan, R.F.D. #1 Burr St., Fairfield, Conn. 06430

[21] Appl. No.: 744,525

[22] Filed: Nov. 24, 1976

[51] Int. Cl.² .............................................. A61C 13/00
[52] U.S. Cl. ................................................................ 32/1
[58] Field of Search ........................... 32/11, 71, 40 R

[56] References Cited

U.S. PATENT DOCUMENTS

| | | | |
|---|---|---|---|
| 3,521,354 | 7/1970 | Stern et al. ................................ | 32/11 |
| 3,931,677 | 1/1976 | Tinder ...................................... | 32/11 |
| 3,952,415 | 4/1976 | Samuel .................................... | 32/11 |

*Primary Examiner*—Robert Peshock
*Attorney, Agent, or Firm*—Arthur T. Fattibene

[57] ABSTRACT

This disclosure is directed to a method of making a dental die and an improved dental dowel pin for facilitating the making of such dental die. The dowel pin comprises a double pronged pin interconnected by a bridge and having an extended portion for locating the pin in a mold cavity prior to the pouring of the die forming material into the mold cavity. The method for making a dental die comprises the step of forming an impression of a patient's teeth to define a mold cavity. The double pronged dowel pin is then inserted into the material of the mold so that the double prongs project upwardly from the mold. The die forming material is poured into the mold cavity in two parts. The first part covering the bridge of the dowel pin to define the dental die, and the second part of the molding material poured on top of the first part to form the mold base when the dental die portion has set, with a lubricant barrier interposed between the two parts. The completed molded part is then removed from the mold cavity whereupon the specific dental die can be cut and separated from the mold base as may be required to form or model a given tooth structure.

1 Claim, 7 Drawing Figures

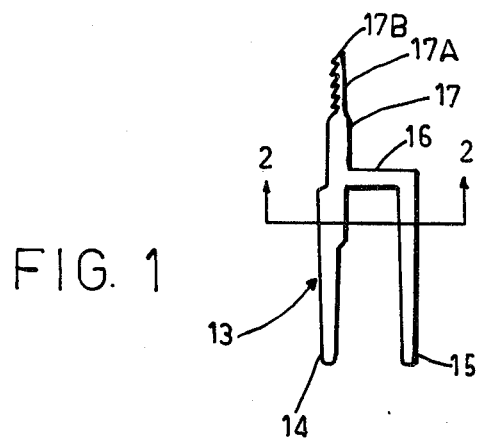
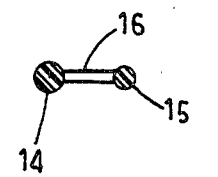
FIG. 1
FIG. 2
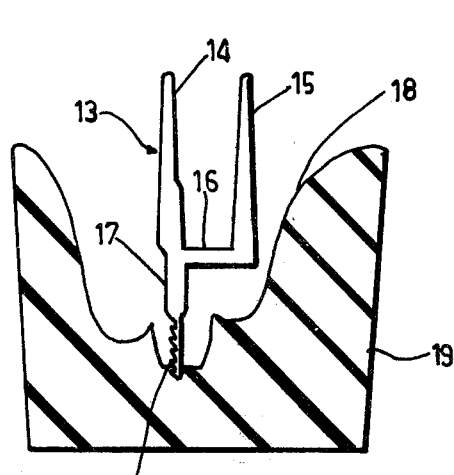
FIG. 3
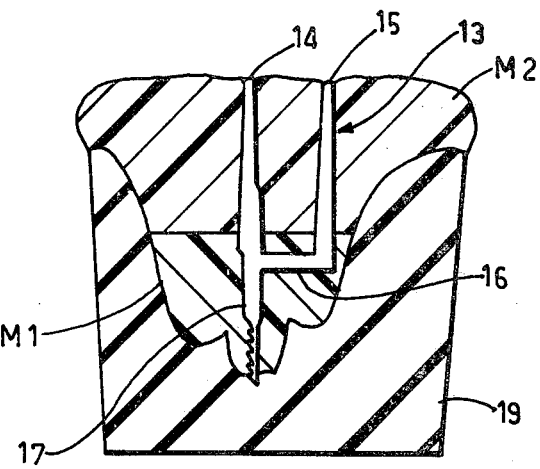
FIG. 4
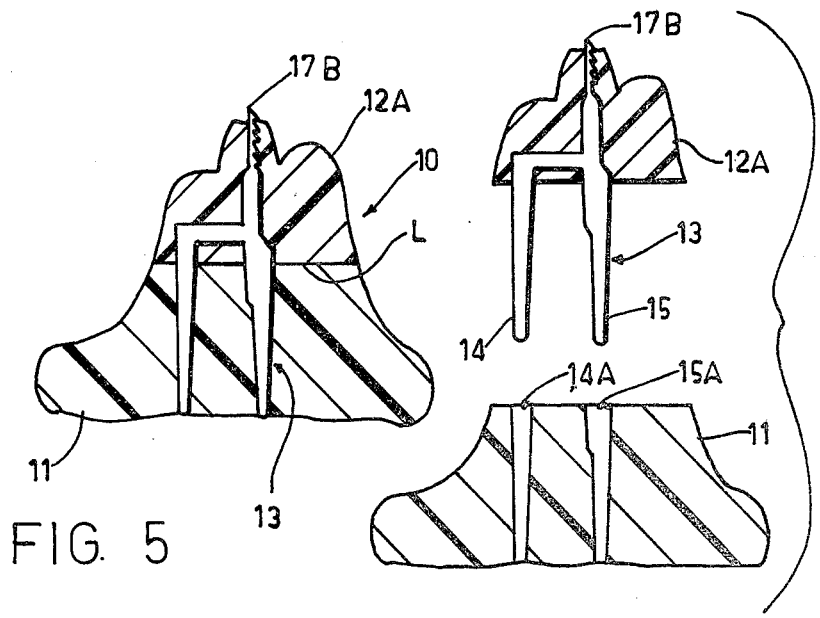
FIG. 5
FIG. 6

IMPROVED DOWEL PIN FOR MAKING A DENTAL DIE

PROBLEM AND PRIOR ART

Dental dies are commonly used in the dental art for making crowns, bridges, inlays, etc. Dental dies comprise a model or form of a tooth which is to be restored, crowned and the like, and which is detachably connected to a mold base which forms the support for the dental die. Heretofore, in the construction of the dental die, a dowel pin was utilized to render the die removeable from the base mold. Such dowel pins consisted of a simple pin about which the mold material of the dental die was permitted to set. However, it has been observed that the use of a simple dowel pin has certain disadvantages in that a die so constructed would tend to rotate relative to its base mold. When ever this occured, the accuracy of the denture, crown, inlay, etc. being made on such die was adversely affected. This was because the simple conventional dowel pin did not provide for positive seating of the dental die relative to the base mold.

OBJECTS

It is therefore an object of this invention to provide an improved dowel pin to facilitate the construction of a dental die.

Another object is to provide an improved dowel pin for insuring the positive seating of a dental die relative to its base mold so as to insure the accuracy of the denture, crown or inlay being formed thereon.

Another object is to provide a dowel pin construction for use with a dental die which prohibits the rotation of the dental die relative to its base mold.

Another object is to provide an improved method for constructing a dental die.

BRIEF SUMMARY OF THE INVENTION

The foregoing objects and other features and advantages are attained by an improved dowel pin and method of making a dental die. The improved dowel pin comprises a double prong pin interconnected by a bridge and having a projection extending beyond the bridge in a direction opposite to the prongs. The projected or extended end is utilized for locating the pin in the mold cavity prior to pouring of the die forming material into the cavity. The double pongs are arranged to extend beyond the dental die and provide the means whereby the dental die can be positively seated relative to the base mold upon which one or more dies are supported.

The method of forming a dental die utilizing the improved dowel pin comprises the step of forming an impression of a patient's teeth to define a mold cavity thereof. The dowel pin is then inserted into the mold so that the dowel prongs project outwardly therefrom. A two part pour is then placed into the cavity; the first part covering the bridge of the dowel pin and allowed to set. The second part is then poured on top of the first part with a lubricant barrier interposed therebetween. When the mold material has set, the completed mold form is removed from the cavity. Cuts are made between the respective dental die portion defined by the first mold part so that the formed dental die can be readily seperated from the base mold part; the projecting prongs serving to provide a positive seating of the dental die relative to the base mold.

FEATURES

A feature of this invention resides in the provision of a dowel pin having spaced apart prongs for use in making dental dies to prohibit any rotation of the dental die relative to the supporting base mold.

Another feature resides in the provision of an improved dowel pin for facilitating the making of accurately positioned and anti-rotating dental dies.

Other features and advantages will become more readily apparent when considered in view of the specification and drawings, in which:

FIG. 1 is a side elevation view of a dental dowel pin embodying the present invention.

FIG. 2 is a sectional view of the dowel pin taken along line 2—2 on FIG. 1.

FIG. 3 is a sectional side view illustrating the positioning of the dowel pin of FIGS. 1 and 2 in a mold cavity prior to pouring of the die forming material.

FIG. 4 is a sectional side view illustrating the position of the dowel pin relative to the mold cavity and the poured dental die forming material.

FIG. 5 is a sectional view of the dental die removed from the mold cavity.

FIG. 6 is an exploded view illustrating the separability of the dental die from its mold base.

DETAILED DESCRIPTION

Figure 7:
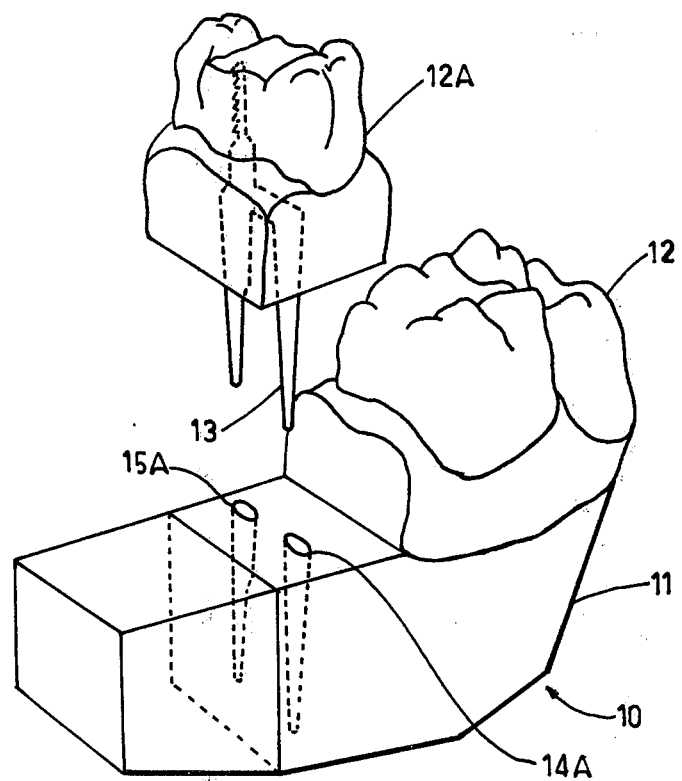
FIG. 7 illustrates a perspective view of the removeable die part relative to the mold base utilizing the improved dowel pin.

Referring to the drawings and more particularly to FIG. 7, there is shown a dental model 10 of a patient's teeth which a dentist or dental laboratory is required to make for teeth restorations, e.g., crowns, inlays, bridges and the like. Such dental models of a patient's teeth comprise essentially of a mold base portion 11 and the dental die portion 12. Depending upon the work to be done, the dental die portion 12 may be separated from the base 11 and adjacent teeth structure, as indicated by die portion 12A. As shown, die portion 12 A comprises the model of a patient's tooth to be restored, e.g., to which a crown is to be fitted. In order to provide for positive seating of the dental die 12A relative to the base mold 11 and adjacent teeth portion, e.g., 12, an improved dowel pin 13 is provided.

Referring to FIGS. 1 and 2, the dowel pin 13 comprises a pair of spaced apart prongs 14 and 15 interconnected by a bridge 16 to define a U-shaped structure. As shown, the respective prongs 14 and 15 are tapered inwardly toward the free ends thereof so as to define a progressive decreasing cross section. Connected to the bridge and extending in a direction opposite to the prongs 14 and 15 is a projection 17. As best seen in FIG. 3, the projection 17 is utilized to locate the dowel pin 13 in a mold cavity 18, which is defined by an impression 19 taken of a patient's teeth.

In the illustrated embodiment, the projection 17 terminates in a serated edge or blade 17A to facilitate the insertion of the dowel pin 13 into the material of the impression 19. However, it will be understood that the projection 17 may terminate with a point or other configuration which will facilitate insertion into the material of the impression to hold the pin 13 in place until the material $M_1$ of the dental die 12 is poured into the mold cavity 18. As shown in FIG. 4, the material forming the dental die 12 is poured into the cavity 18 to a level sufficient to cover the bridge 16. When the material $M_1$ of the die portion 12 has set, a second material M2 is poured into the cavity on top of the die material M1 to define the base mold portion 11 of the model or mold 10.

Upon setting of the base mold material M2, the model 10 is removed from the cavity 18 of impression 19. With the model or mold 10 removed from the cavity 18, the dentist or laboratory technician can cut or saw the desired die part, e.g., 12A from the rest of the mold whereby the dentist can form the necessary restoration on the die portion and periodically reset the same to the model or mold 10 to insure proper fit when the restored portion or crown and the like is placed in the patient's mouth. The arrangement is such that the die portion 12A can be readily separated at the line L defining the dental die 12 and the base mold 11. As it will be hereinafter described, the integrity of the dental die 12 and base mold 11 can be maintained by providing a separating barrier between the two pours M1 and M2 in forming the model 10.

Because of the tapered of prongs 14 and 15, it will be noted in viewing FIGS. 5 and 6 that the dental die 12A can be readily lifted off of the base portion. Also, the die portion can be readily and accurately reseated to the base portion by the positioning of prongs 14 and 15 into the seats 14A and 15A formed in the base mold.

In accordance with this invention, the dowel pin 13 is integrally formed of a suitable plastic material, e.g., Zytel Nylon, or a glass filled nylon or other suitable plastic. Because the dowel pin is formed of plastic, it will be understood that the top end 17B which may project beyond the top of the dental die 12A can be readily cut off by a hot spatula or other suitable cutting tool so that the top of the die member 12A may conform exactly to the shape of the patient's tooth. The removal of the exposed tip 17B of the dowel pin results in a dental die which conforms to the patient's tooth to be restored.

Because of the double pronged dowel pin 13, which is integrally made part of the dental die 12A and arranged to snugly conform to the seats 14A, 15A which were initially defined by the prongs 14 and 15, the positive accurate and non-rotating seating of the dental die 12A to the mold base 11 is insured. Thus a dentist or laboratory technician can repeatedly remove the dental die 12A in making the necessary restoration and at the same time can be assured that the dental die can be accurately reseated each time. With the dowel pin described, more accurate restorations can be had. The accuracy provided further reduces the time otherwise required for the dentist to place the restoration in the patient's mouth, since less fitting time is required.

The method for making dental molds or dies utilizing the dowel pin 13 comprises the step of first taking an impression 19 of a patient's teeth using a rubber or wax base material. The impression 19 when set is then removed from the patient's teeth. With the impression 19 removed, a dowel pin 13 is inserted into the material of the impression 19, as best seen in FIG. 3. The first mold material M1 is poured into the cavity 18 to a level sufficient to cover the bridge 16 of the dowel pin 13. The material M1 is then allowed to set. Upon setting of Material M1, a layer of a suitable lubricant, e.g., vasoline is coated onto the surface of the set material M1. A second pour of the base forming Material M2 is then poured onto the first set material M1 to an extent sufficient to surround the upstanding prongs 14 and 15 of pin 13. When the material M2 has set, the completed molded structure comprising of Materials M1 and M2 is removed from the impression 19. Referring to FIG. 7, the molded part comprises a base portion 11 having mounted thereon one or more teeth dies 12 and 12A depending upon a given teeth restoration situation. Where more than one tooth die 12 is formed, the respective tooth dies can be readily separated by the dentist or die technician forming a saw cut between tooth dies to the demarcation line L between the die 12 and base 11. The respective tooth die, e.g., 12A is now rendered readily separable from the mold base 11 due to the lubricant barrier. Also the separated tooth die, e.g., 12A can be readily replaced to the base in an accurate manner due to the projecting prongs 14 and 15 which are accurately fitted to seats 14A and 15A in the base mold 11. The tapered configuration of prongs 14 and 15 facilitate the removal of the die, e.g., 12A by pushing up on the bottom of the prongs 14 and 15 with a sharp instrument, if necessary. In the event that the tip 17B of the dowel pin projects beyond the surface of the tooth die, e.g., in 12A, the extended portion 17B can be cut or severed off with a hot spatula. In this manner a perfectly formed tooth die of a tooth restoration can be made. The appropriate crown, bridge, inlay, etc. can then be formed onto the tooth die 12A, and tested with respect to the remainder of the teeth formation on a model 10. As the dowel pin described prohibits any relative rotation of the tooth die 12A relative to the remainder of the teeth model 10, accurate construction of the restoration crown, inlay, bridge etc., can be made so that when the same is ready for insertion into a patient's mouth, a proper fit is assured with a minimum of time lost.

While the method of forming a dental die mold and a dowel pin construction for facilitating the making thereof has been described with respect to a particular embodiment, it will be understood and appreciated that variations and modifications may be made without departing from the spirit or scope of the invention.

What is claimed is:

1. A dowel pin for facilitating the construction of a dental die comprising:
   a unitary member formed of a plastic material having a U-shaped portion having opposed leg members to define spaced apart prongs and a bridge interconnecting said prongs,
   and an extended end projection to define a locating blade connected to and projecting beyond said bridge in a direction opposite to the direction of said spaced apart prongs,
   said locating blade having a surrated edge,
   said blade terminating in an end portion which is adapted to be inserted into the material defining an impression cavity for forming a dental die to locate and maintain the pin within said impression cavity,
   said dowel pin being dimensioned so that the bridge portion is embedded in the dental die portion and the spaced prongs extend from the die portion so as to be detachably secured to the support base portion of the dental die.

* * * * *